United States Patent [19]

Terao et al.

[11] Patent Number: 4,925,976
[45] Date of Patent: May 15, 1990

[54] OLEFIN SULFONATION METHOD

[75] Inventors: Toshimi Terao, Chiba; Kentaro Kiyama, Chofu; Kyozo Kitano, Narashino, all of Japan

[73] Assignee: Lion Corporation, Tokyo, Japan

[21] Appl. No.: 843,838

[22] Filed: Mar. 26, 1986

Related U.S. Application Data

[63] Continuation of Ser. No. 616,025, May 31, 1984, abandoned.

[30] Foreign Application Priority Data

May 31, 1983 [JP] Japan .................................. 58-096725

[51] Int. Cl.$^5$ ........................................... C07C 143/02
[52] U.S. Cl. .................................................. 562/123
[58] Field of Search ........................ 260/504 R, 513 P; 562/123

[56] References Cited

U.S. PATENT DOCUMENTS 3,781,339  12/1973  Tuvell et al. .................... 260/513 T
3,808,157   4/1974  Dewitt et al. ................... 260/513 T Primary Examiner—Alan Siegel
Attorney, Agent, or Firm—Armstrong, Nikaido, Marmelstein, Kubovcik & Murray

[57] ABSTRACT

A method for sulfonating olefins comprising the steps of mixing (A) internal olefins having 8 to 22 carbon atoms with (B) alpha-olefins having an average carbon atom number, larger by 3 to 7 than that of the internal olefins (A) in a weight ratio of (A)/(B)=95/5 to 5/95, and sulfonating the resultant mixture with a sulfonating agent. Thus, internal olefins can be sulfonated at a high conversion.

3 Claims, No Drawings

OLEFIN SULFONATION METHOD

This application is a continuation of application Ser. No. 616,025 filed May 31, 1984 now abandoned.

BACKGROUND OF THE INVENTION

1. Field of the Invention

The present invention relates to a method for sulfonating olefins. More specifically, it relates to a method for sulfonating olefins in which the sulfonation efficiency of internal olefins is improved.

2. Description of the Prior Art

Internal olefin sulfonates are known as surfactants having excellent penetrating power and low temperature stability. However, they have not been generally used due to production problems. That is, alpha-olefins having structures similar to those of internal olefins have a high reactivity to sulfur trioxide $SO_3$ and readily form alpha-olefin sulfonates. However, although a sulfonation efficiency of internal, olefins having 8 to 14 carbon atoms is up to approximately 94% by weight, the reactivity, to $SO_3$, of internal olefins having more than 15 carbon atoms is remarkably decreased and the conversion is at most approximately 89%, even when various attempts to increase the reactivity, for example, the increase in the $SO_3$ mol ratio are made For this reason, a large amount of unreacted oil (i.e., olefins) remains in the sulfonated products, which cannot be directly utilized in various application fields such as detergent compositions.

Various attempts have been made to solve these problems. For example, U.S. Pat. No. 4,183,867 proposes a two-step sulfonation method in which the unreacted oil is further reacted by adding sodium sulfonate thereto, followed by the addition of sulfuric acid to effect the sulfonation. Japanese Unexamined Patent Publication (Kokai) No. 54-14918 proposes extraction of the unreacted oil with a solvent, to recover the unreacted oil. U.S. Pat. No. 3,893,940 proposes recovery of the unreacted oil by stripping. However, the above-mentioned two-step sulfonation method in which sodium sulfate is added is disadvantageous in that the resultant products are limited in their utility fields due to the increase in the inorganic contents. The above-mentioned methods for separating the unreacted oil by solvent extraction or stripping are not preferable from the economical point of view since the separation and recovery steps of the unreacted oil are complicated. Furthermore, the use of solvents causes difficulty in the complete removal of the solvents from the resultant products, and increases costs due to the use of the solvents.

SUMMARY OF THE INVENTION

Accordingly, the objects of the present invention are to eliminate the above-mentioned disadvantages of the prior art and to provide a method for sulfonating internal olefins at a high conversion.

Other objects and advantages of the present invention will be apparent from the following description.

In accordance with the present invention, there is provided a method for sulfonating olefins comprising the steps of: mixing (A) internal olefins having 8 to 22 carbon atoms with (B) alpha-olefins having an average carbon atom number larger by 3 to 7 than that of the internal olefins (A) in a weight ratio of (A)/(B)=95/5 to 5/95; and sulfonating the resultant mixture with a sulfonating agent.

DESCRIPTION OF THE PREFERRED EMBODIMENTS

The internal olefins (A) used as a starting material in the present invention are those having 8 to 22 carbon atoms, preferably 10 to 20 carbon atoms. Typical examples of the internal olefins are those having the general formula:

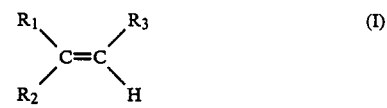

wherein $R_1$ and $R_3$ are independently linear or branched alkyl groups and $R_2$ is hydrogen or a linear or branched alkyl group, provided that the total carbon atom number of $R_1$, $R_2$, and $R_3$ is 6 to 20.

These internal olefins can be readily available as dimers (i.e., dimer olefin), which are obtained from the dimerization of olefins having 4 to 11 carbon atoms. Preferable internal olefins used in the present invention are those represented by the general formula (I) in which $R_2$ is hydrogen. These preferable internal olefins generally have double bond linkage position distributions such that 1-position is 0%, 2-position 10% to 30%, 3-position 10% to 30%, 4-position 10% to 30%, 5-position 5% to 20%, 6-position 5% to 15%, and 7-position and the inner position thereof 0% to 15%.

According to the present invention, alpha-olefins (B) having an average carbon atom number larger by 3 to 7, preferably 3.3 to 6, than that of the internal olefins (A) are added to the internal olefins (A) prior to the sulfonation. When the average carbon atom numbers of the internal olefins (A) and the alpha-olefins (B) are equal to each other, the alpha-olefins (B) are sulfonated in preference to the internal olefins (A), because the reactivity of the alpha-olefins (B) to $SO_3$ is higher than that of the internal olefins (A). Thus, the sulfonation conditions are not substantially changed when compared to those under which the internal olefins (A) are sulfonated alone. Therefore, the sulfonation efficiency is not improved. When the average carbon atom number of the alpha-olefins (B) is too large when compared with that of the internal olefins (A), the internal olefins (A) are sulfonated in preference to the alpha-olefins (B) and, therefore, the sulfonation efficiency of the internal olefins (A) is not improved as mentioned above.

Contrary to the above, when the average carbon atom number of the internal olefins (A) is larger by 3 to 7 than that of the alpha-olefins (B), the sulfonation efficiency of th internal olefins (A) is increased by 4% to 7% when compared with the sulfonation of the internal olefins (A) alone. It is believed that this is due to the fact that the sulfonation rate of the internal olefins (A) is substantially the same as that of the alpha-olefins (B) and, therefore, the sulfonation of the internal olefins (A) and the alpha-olefins (B) proceeds concurrently, although the actual mechanism is not known. In this case, the conversion of the alpha-olefins (B) is substantially the same as that when the alpha-olefins alone are sulfonated. The alpha-olefins (B) can be prepared by, for example, an ethylene polymerization or wax cracking method.

According to the present invention, the internal olefins (A) must be mixed with the alpha-olefins (B) in a weight ratio of (A)/(B)=95/5 to 5/95, preferably 80/20 to 20/80. When the weight ratio of (A)/(B) is less than 95/5, the above-mentioned addition effect of the alpha-olefins (B) is not well exhibited. Contrary to this, when the ratio (A)/(B) is more than 5/95, the economical merit cannot be effected since the internal olefin content is small.

The sulfonation according to the present invention can be carried out in any known manner by using any conventional sulfonating agents such as gaseous $SO_3$, liq. $SO_3$, and oleum.

Typical sulfonating conditions when gaseous $SO_3$ is used are as follows:

Reaction method: A thin film type continuous sulfonating method
$SO_3$: A mixture of $SO_3$ and an inert gas ($SO_3$/an inert gas=1% to 10% by volume, preferably 1% to 5% by volume)
$SO_3$/starting material (molar ratio): 1.0 to 2.0
Reaction temperature: 30° C. to 80° C.

After the sulfonation, the sulfonated products are generally neutralized at a temperature of, for example, 40° C. to 80° C. by adding an alkaline solution such as a 40% aqueous alkaline solution (e.g., NaOH, KOH, and alkanol amines). The neutralized products are then hydrolyzed at a temperature of 100° C. to 180° C. for 5 minutes to 7 hours to obtain mixtures of internal olefin sulfonates and alpha-olefin sulfonates.

According to the present invention, the sulfonated products can be directly utilized as a surfactant in various application fields without necessitating the removal of the unreacted oil, since the conversion of the internal olefins is high. Especially, when the sulfonated products are intended to be used as a surfactant in a so-called enhanced oil (or petroleum) recovery method, excellent oil recovery can be advantageously and readily obtained by changing the mixing ratio of the internal olefin sulfonates and the alpha-olefin sulfonates depending upon an inorganic salt concentration of the brine available in subterranean oil reservoirs. This is because the desired effect of the internal olefin sulfonates is exhibited at a low inorganic salt concentration of the brine, and the desired effect of the alpha-olefin sulfonates is exhibited at a relatively high salt concentration of the brine.

EXAMPLES

The present invention now will be further illustrated by, but is by no means limited to, the following Examples.

EXAMPLE 1

The following olefins were used as starting materials:
$C_{156}IO$: Linear internal olefin having a composition of 5% of $C_{14}$, 40% of $C_{15}$, 50% of $C_{16}$, and 5% of $C_{17}$, an average carbon atom number of 15.6, and a double bond position distribution of 0% of 1-position, 24% of 2-position, 17% of 3-position, 16% of 4-position, and 43% of 5-position or more;
$C_{146}AO$: Alpha-olefin having a composition of 20% of $C_{14}$ and 80% of $C_{16}$ and an average carbon atom number of 15.6; and
$C_{202}AO$: Alpha-olefin having a composition of 57% of $C_{20}$ and 43% of $C_{22}$ and an average carbon atom number of 20.9;

wherein no internal olefin was included in $C_{146}AO$ and $C_{202}AO$, IO and AO represent internal olefin and alpha-olefin, respectively, and $C_{22}$ represents an olefin having 22 carbon atoms.

Various combinations of the above starting olefins were sulfonated in a laboratory-scale continuous thin film type sulfonation apparatus. This sulfonation apparatus was made of pyrex glass and had an inner diameter of 6 mm and a reactor length of 1.5 m. The starting olefins and an $NSO_3$-inert gas (i.e., $N_2$) were downwardly flowed in a parallel flow manner through the sulfonation apparatus to place than in contact with each other under the following reaction conditions:

$SO_3$/Starting olefins (molar ratio): 1.5
$SO_3$ concentration in the mixture of $SO_3$ and inert gas: ($N_2$) 2.8%
Starting olefin feed rate: 3 g/minutes
Reaction temp.: 50° C.

The sulfonated products thus obtained were neutralized by adding a 35% aqueous sodium hydroxide solution in such an amount that the amount of the sodium hydroxide was at least equimolar with the sulfonated products. The neutralized products were then hydrolyzed at a temperature of 160° C. for 20 minutes to form sulfonate compositions.

The amounts of the internal olefins and the alpha-olefins were determined by a gas chromatograph analysis and the conversions were determined.

The results are shown in Table 1.

TABLE 1

|  | Present example | Comparative example | | |
|---|---|---|---|---|
| Starting olefin | $C_{156}IO/C_{202}AO$ | $C_{156}IO/C_{146}AO$ | $C_{156}IO$ | $C_{202}AO$ |
| Difference in average C number *1 | 5.3 | 0 | — | — |
| Mixing ratio (A)/(B) *2 | 5/5  8/2 | 8/2 | 10/0 | 0/10 |
| Conversion (%) *3 | 94/96  94/95 | 88/97 | 88 | 95 |

*1: Average carbon atom number of component (A) - average carbon atom number of component (B)
*2: Weight ratio
*3: Sulfonation efficiency of component (A)/sulfonation efficiency of component (B)

As is clear from the results shown in Table 1, according to the present invention, the conversion of the internal olefins is readily increased.

EXAMPLE 2

The following olefins were used as starting materials:
$C_{134}IO$: Linear internal olefin having a composition of 0.2% of $C_{12}$, 54% of $C_{13}$, and 45.8% of $C_{14}$, an average carbon atom number of 13.5, and a double bond position distribution of 0% of 1-position, 25% of 2-position, 22% of 3-position, 15% of 4-position, and 38% of 5-position or more;
$C_{14}AO$: Alpha-olefin comprising 100% of $C_{14}$;
$C_{168}AO$: Alpha-olefin having a composition of 50% of $C_{16}$ and 50% of $C_{18}$ and an average carbon atom number of 17;

wherein no internal olefin was included in $C_{14}AO$ and $C_{168}AO$.

The above starting olefins were sulfonated in the same manner as in Example 1, except that a molar ratio of $SO_3$/the starting olefin was changed to 1.2.

The results are shown in Table 2.

TABLE 2

| | Present example | | | Comparative example | |
|---|---|---|---|---|---|
| Starting olefin | $C_{134}IO/C_{168}AO$ | | | $C_{134}IO/C_{14}AO$ | $C_{134}IO$ |
| Difference in average C number *1 | 3.5 | | | 0.5 | — |
| Mixing ratio (A)/(B) *2 | 8/2 | 5/5 | 3/7 | 8/2 | 10/0 |
| Conversion (%) *3 | 99/95 | 98/95 | 98/95 | 94/97 | 94 |

*1, *2, and *3: same as in Table 1.

As is clear from the results shown in Table 2, according to the present invention, even when the internal olefins having 14 or less carbon atoms are sulfonated, the conversion is further improved.

We claim:

1. A method for sulfonating olefins comprising the steps of:

mixing (A) internal olefins having 8 to 22 carbon atoms with (B) alpha-olefins having an average carbon atom number larger by 3 to 7 than that of the internal olefins (A) in a weight ratio of (A)/(B)=95/5 to 5/95; and sulfonating the resultant mixture with, as a sulfonating agent, at least one of liquid sulfur trioxide or gaseous sulfur trioxide.

2. A method as claimed in claim 1, wherein the internal olefins are those having the general formula:

wherein $R_1$ and $R_3$ are independently linear or branched alkyl groups and $R_2$ is hydrogen or a linear or branched alkyl group, provided that the total carbon atom number of $R_1$, $R_2$, and $R_3$ is 6 to 20.

3. A method as claimed in claim 1, wherein the weight ratio of the component (A) to the component (B) is within the range of from 80/20 to 20/80.

* * * * *